(12) United States Patent
Howie et al.

(10) Patent No.: US 10,080,913 B2
(45) Date of Patent: Sep. 25, 2018

(54) FILTER BOX ASSEMBLY AND FILTER UNIT

(76) Inventors: Robin Middlemass Howie, Edinburgh (GB); Derek Mervyn Robinson, London (GB)

(*) Notice: Subject to any disclaimer, the term of this patent is extended or adjusted under 35 U.S.C. 154(b) by 1012 days.

(21) Appl. No.: 14/235,163

(22) PCT Filed: Jul. 27, 2012

(86) PCT No.: PCT/GB2012/051838
§ 371 (c)(1),
(2), (4) Date: Jul. 2, 2014

(87) PCT Pub. No.: WO2013/014472
PCT Pub. Date: Jan. 31, 2013

(65) Prior Publication Data
US 2014/0366883 A1    Dec. 18, 2014

(30) Foreign Application Priority Data

Jul. 27, 2011    (GB) .................................. 1112917.8

(51) Int. Cl.
*B01D 53/02*    (2006.01)
*A62B 23/02*    (2006.01)
(Continued)

(52) U.S. Cl.
CPC ......... *A62B 23/02* (2013.01); *A61M 16/0825* (2014.02); *A61M 16/105* (2013.01);
(Continued)

(58) Field of Classification Search
CPC ............ A61M 16/0825; A61M 16/105; A61M 16/107; B01D 2253/102; B01D 2253/106;
(Continued)

(56) References Cited

U.S. PATENT DOCUMENTS 4,543,112 A    9/1985    Ackley et al.
5,720,280 A    2/1998    Elstran et al.
(Continued)

FOREIGN PATENT DOCUMENTS

WO    99/12635 A1    3/1999

OTHER PUBLICATIONS

International Search Report and Written Opinion of related PCT/GB2012/051838.

*Primary Examiner* — Christopher P Jones
(74) *Attorney, Agent, or Firm* — Benesch, Friedlander, Coplan & Aronoff LLP

(57) ABSTRACT

A filter unit for use in a filter box assembly, the filter unit comprising a particulate filter layer and a gas filter layer, the particulate filter layer being configured to bias towards the gas filter layer, exerting pressure thereon. There is also described filter box assemblies (including a duel filter assembly) comprising the filter unit, and a respiratory protective device comprising the filter unit. Also described is a method of manufacturing a filter unit with a gas filter layer and a particulate filter layer, wherein a force is applied to the particulate filter layer causing it to fix the gas filter layer in place. Also described is a method of manufacturing a dual filter assembly wherein a casing is twice reversibly attached to and detached from a support surface, filter units being added to the casing when the casing is attached to the surface.

12 Claims, 3 Drawing Sheets

(51) Int. Cl.
*B01D 46/00* (2006.01)
*B01D 46/10* (2006.01)
*B01D 53/04* (2006.01)
*A62B 19/00* (2006.01)
*A61M 16/10* (2006.01)
*A61M 16/08* (2006.01)
*A62B 7/10* (2006.01)

(52) U.S. Cl.
CPC .......... A61M 16/107 (2014.02); A62B 19/00 (2013.01); B01D 46/002 (2013.01); B01D 46/0015 (2013.01); B01D 46/0026 (2013.01); B01D 46/0032 (2013.01); B01D 46/0036 (2013.01); B01D 46/0091 (2013.01); B01D 46/10 (2013.01); B01D 53/0415 (2013.01); *A62B 7/10* (2013.01); *B01D 2253/102* (2013.01); *B01D 2253/106* (2013.01); *B01D 2253/108* (2013.01); *B01D 2253/116* (2013.01); *B01D 2257/90* (2013.01); *B01D 2257/93* (2013.01); *B01D 2258/06* (2013.01); *B01D 2259/4541* (2013.01); *B01D 2259/4583* (2013.01); *B01D 2265/028* (2013.01); *B01D 2267/30* (2013.01); *Y10T 29/49826* (2015.01)

(58) Field of Classification Search
CPC .......... B01D 2253/108; B01D 2257/90; B01D 2257/93; B01D 2258/06; B01D 2259/4541; B01D 2259/4583; B01D 2265/028; B01D 2267/30; B01D 46/0015; B01D 46/002; B01D 46/0026; B01D 53/0415; B01D 2253/116; B01D 46/0032; B01D 46/0036; B01D 46/0091; B01D 46/10; Y10T 29/49826; A62B 19/00; A62B 23/02; A62B 7/10

See application file for complete search history.

(56) References Cited

U.S. PATENT DOCUMENTS

| | | |
|---|---|---|
| 6,119,689 A | 9/2000 | Korman |
| 7,861,719 B1 | 1/2011 | Grove et al. |

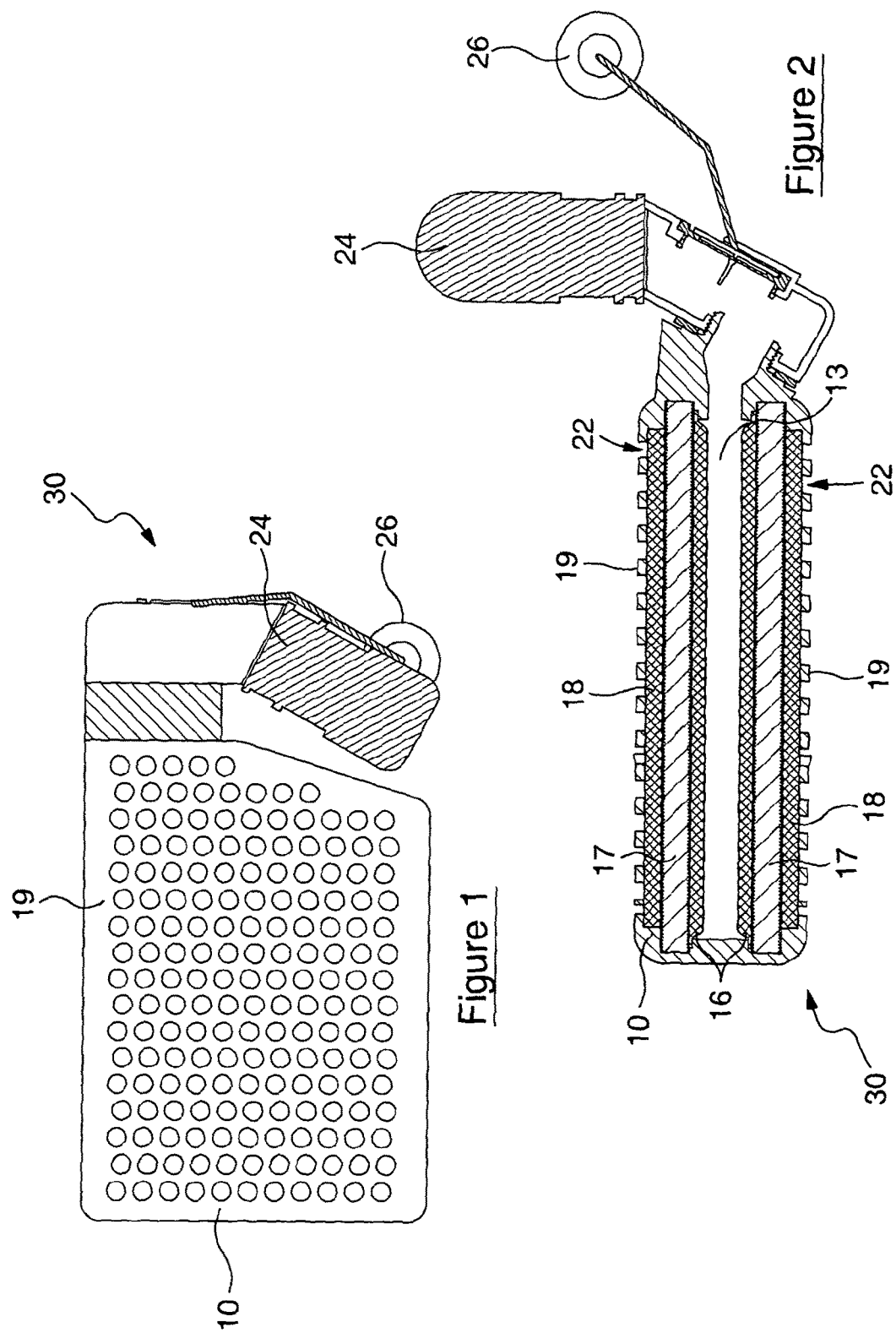

FILTER BOX ASSEMBLY AND FILTER UNIT

CROSS-REFERENCE TO RELATED APPLICATIONS

This application is a National stage entry under 35 U.S.C. § 371 of PCT Patent Application No. PCT/GB2012/051838, filed Jul. 27, 2012, which claims priority to United Kingdom Patent Application No. GB 1112917.8, filed on Jul. 27, 2011, each of which is hereby incorporated by reference.

FIELD OF THE INVENTION

The present invention relates generally to a filter box assembly and a method of manufacture thereof, and in particular to filter box assembly for use with or in a respiratory protective device. In one aspect the present invention relates to a filter unit and a method of manufacture thereof, and in particular to a filter unit for use with or in a filter box assembly.

BACKGROUND OF THE INVENTION

A number of respiratory protective devices are fitted with filter box assemblies and/or filter units. The filter box assemblies and/or filter units are ordinarily connected to a facepiece, such as a half-mask or a mouthpiece, which provides an effectively airtight connection between the breathing zone or mouth of the wearer of the device and the filter box assembly/filter unit. This ensures that the user can only breathe air which has been filtered to remove contaminants including, for example, toxic gases and particulates.

As noted above, respiratory protective devices often need to be used when there is the presence of airborne hazardous substances. However, in such situations many users find that the breathing resistance of the devices makes them extremely uncomfortable to use, to the extent that some would-be users refuse to wear such equipment. Such situations most typically occur where the users are required to carry out high energy work; where the users are unfamiliar with wearing respirators or protective devices; or where the users are scared or anxious (for example, when using the device for self-rescue).

If users consider the devices to be too uncomfortable, they may refuse to wear them or they may wear the devices incorrectly in an attempt to minimise discomfort. In such cases the wearers may be provided with no, or substantially reduced, respiratory protection against the airborne hazardous substances of concern.

Attempts have been made to provide respiratory protective devices with breathing resistances that are acceptable to the majority of wearers in the majority of situations. The breathing resistance in such devices is based on national and international standards, which specify upper limits for breathing resistance. However, these standards were drafted and set several decades ago. Thus, current such limits are based on what could have been achieved using historical filter technologies, albeit they were current when the national and international standards were drafted. It would, of course, be of more use to design modern filters based on physiological data as to the subjective acceptability of the imposed breathing resistances of respiratory protective devices.

In order to minimise breathing resistance, the size of filters used in respiratory protective devices can be increased and/or multiple filters may be used. Although devices with large or multiple filters will have a lower breathing resistance than devices fitted with single filters of normal size, the use of larger or multiple filters increases the bulk and weight of the devices. Such increased bulk and weight is disadvantageous, particularly for devices which must be carried on the body, or stored in large numbers close to sites of potential use.

Furthermore, there is an express need in some instances for devices to be even more compact than existing devices. For example, there are instances where respiratory protective devices are required to be compact in order to be inconspicuous or easily carried about the person for self-rescue.

Many respiratory protective devices contain both particulate filters and gas (or vapour) filters. Both the particulate and gas filters used have to meet technical requirements as to their protective performance and/or capacity against the agents of concern. Therefore, such devices have a set minimum volume of gas and vapour absorbents/adsorbents, and a set minimum area of particulate filter media that is required such that they comply with the relevant national or international standards.

In an attempt to address some of the problems highlighted above, a number of devices have used "double-sided filters", i.e. filter assemblies where two or more filter sub-units feed into a single clean air channel, as a means of minimising breathing resistance while enhancing the protective performance of the particulate filters. However, although technically effective, such double-sided filters can be awkward to manufacture to the required standards of quality; particularly if the gas and vapour filter beds are of shallow depth, e.g. of less than about 10 mm depth.

Conventional gas and vapour filters incorporate loose granules of adsorbents/absorbents. When using such filters, it is necessary to apply a force to the granule bed to lock the granules in position so that the granules do not rub against each other, abrade and/or slump, so forming voids through which gases or vapours can pass without being retained by the adsorbents/absorbents. Such force is usually generated by incorporating some form of spring mechanism. This makes such filters difficult to manufacture and, inevitably, adds to the overall bulk. This is particularly the case when building a filter assembly with more than one filter unit.

There is therefore a need for a simple and reliable means of manufacturing compact double-sided, or other multi-sided, filter box assemblies that contains gas (vapour) and particulate filters.

There is also a need for a compact filter unit having a gas and a particulate filter layer at least, and a simple and reliable means of manufacturing such a compact filter unit and an associated filter box assembly.

Therefore, it is an object of the present invention to obviate, or at least mitigate, at least some of the drawbacks associated with the prior art.

Further aims and objects of the invention will become apparent from a reading of the following description.

SUMMARY OF THE INVENTION

According to a first aspect of the invention there is provided a filter box assembly for use with a respiratory protective device, said filter box assembly comprising a first filter unit and a second filter unit, wherein the first and second filter units share a common air channel in fluid contact therewith.

The first and second filter units may be configured to be substantially parallel.

The common air channel may be located between the first and second filter units.

The filter box assembly may further comprise a spacer configured to space apart the first filter unit and the second filter unit. The depth of the common air channel may be defined by the spacer.

Typically the common air channel is adjacent the first and second filter units.

Preferably the common air channel is in direct contact with the first and second filter units.

The common air channel may be configured to be substantially parallel with the first and second filter units.

The filter unit may comprise a gas filter layer.

The filter unit may comprise a first particulate filter layer.

The filter unit may comprise a support layer. The support layer may be a second particulate filter layer.

The gas filter layer may be located between the first particulate filter layer and the support layer.

The gas filter layer may be adjacent the first particulate filter layer and the support layer.

Preferably the gas filter layer is in direct contact with the first particulate filter layer and the support layer.

The gas filter layer may be configured to be substantially parallel with the first particulate filter layer.

The gas filter layer may be configured to be substantially parallel with the support layer.

The filter unit may comprise a perforated support plate; typically a first perforated support plate and a second perforated support plate.

The first particulate filter layer may be located between the first perforated support plate and the second perforated support plate.

The first particulate filter layer may be adjacent one of the perforated support plates.

The first particulate filter layer may be in direct contact with one of the perforated support plates.

The support layer may be located between the first perforated support plate and the second perforated support plate.

The support layer may be adjacent one of the perforated support plates.

The support layer may be in direct contact with one of the perforated support plates.

The first particulate filter layer may be configured to be substantially parallel with the first and second perforated support plates.

The support layer may configured to be substantially parallel with the first and second perforated support plates.

Preferably the particulate filter layer is configured to bias towards the gas filter layer.

The particulate filter layer may be located on the influent side of the gas filter layer.

Preferably the particulate filter layer comprises a resilient material.

Preferably the particulate filter layer is compressed such that it applies a positive force against the gas filter layer.

According to a second aspect of the invention there is provided a respiratory protective device comprising a filter box assembly as described in the first aspect.

According to a third aspect of the invention, there is provided a method of manufacturing a filter box assembly comprising the steps of:

i. providing a casing configured to accommodate at least a first and a second filter unit, said casing comprising an air channel common to the first and second filter units and in fluid contact therewith;

ii. providing a first filter unit to the casing; and iii. providing a second filter unit to the casing.

The filter box assembly may further comprise a spacer configured to space apart the first filter unit and the second filter unit. The depth of the common air channel may be defined by the spacer.

The method may comprise the further steps of:

i. reversibly attaching the casing to a support surface before providing the first filter unit to the casing;

ii. detaching the casing from the support surface after provision of the first filter unit;

iii. reversibly attaching the casing or a lid to a support surface before providing the second filter unit to the casing; and iv. detaching the casing or the lid from the support surface after provision of the second filter unit.

Attachment to the support surface may be via a lid of other suitable part of the assembly.

The method may comprise the further steps of:

i. providing a first perforated support plate to the inside of the casing, so as to abut the spacer;

ii. providing a support layer to the inside of the casing and in contact with the first perforated support plate;

iii. providing a gas filter layer to the inside of the casing and in contact with the support layer;

iv. providing a first particulate filter layer to the inside of the casing in contact with the gas filter layer; and v. providing a second perforated support plate to the inside of the casing and in contact with the first particulate filter layer.

The particulate filter layer may be located on the influent side of the gas filter layer.

Preferably the support layer is a second particulate filter layer.

The method may comprise the further step of applying a force to the first particulate filter layer thereby causing a force to be applied to the gas filter layer, fixing said gas filter layer in place.

Preferably the force is applied to the second perforated support plate, which applies a force to the first particulate filter layer thereby causing a force to be applied to the gas filter layer, fixing said gas filter layer in place.

Preferably the force applied causes the particulate filter layer to compress and to apply a force on the gas filter layer.

The force applied may be approximately 50 kg (490 N).

Therefore, in one aspect the present invention describes a novel technique for the manufacture of filters (filter box assemblies) for use in (personal) respiratory protective equipment, said filter box assemblies having low airflow resistance.

According to a fourth aspect of the invention there is provided a filter box assembly manufactured by the method of the third aspect.

According to a fifth aspect of the invention there is provided a filter unit for use in a filter box assembly, said filter unit comprising at least a first particulate filter layer and a gas filter layer, wherein the particulate filter layer is configured to bias towards the gas filter layer.

The particulate filter layer may be located on the influent side of the gas filter layer.

Preferably the particulate filter layer comprises a resilient material.

Preferably the particulate filter layer is compressed such that it applies a positive force against the gas filter layer.

The force applied may be approximately 50 kg (490 N).

Force can be generated by compressing the particulate filter medium (layer) and using the compressed filter as a "spring" where the nature of the medium has suitable characteristics.

Where the particulate filter medium is formed from electrostatically charged fibres, compression of the particulate filter can increase the efficiency with which the filter collects particulates, so enhancing the performance of the particulate filter.

The filter unit may comprise a support layer.

Preferably the support layer is a second particulate filter layer.

The gas filter layer may be located between the first particulate filter layer and the support layer.

The gas filter layer may be adjacent the first particulate filter layer and the support layer.

The gas filter layer may be in direct contact with the first particulate filter layer and the support layer.

The gas filter layer may be configured to be substantially parallel with the first particulate filter layer.

The gas filter layer may be configured to be substantially parallel with the support layer.

Preferably the filter unit comprises a perforated support plate.

The filter unit may comprise a first perforated support plate and a second perforated support plate.

The first particulate filter layer may be located between the first perforated support plate and the second perforated support plate.

The first particulate filter layer may be adjacent one of the perforated support plates.

The first particulate filter layer may be in direct contact with one of the perforated support plates.

The support layer may be located between the first perforated support plate and the second perforated support plate.

The support layer may be adjacent one of the perforated support plates.

The support layer may be in direct contact with one of the perforated support plates.

The first particulate filter layer may be configured to be substantially parallel with the first and second perforated support plates.

The support layer may be configured to be substantially parallel with the first and second perforated support plates.

According to a sixth aspect of the invention there is provided a filter box assembly comprising the filter unit of the fifth aspect.

According to a seventh aspect of the invention there is provided a respiratory protective device comprising a filter unit as described in the fifth aspect, or the filter box assembly as described in the sixth aspect.

According to an eighth aspect of the invention there is provided a method of manufacturing a filter unit comprising the steps of:

i. providing a casing configured to accommodate the components of a filter unit;
ii. providing a gas filter layer to the inside of the casing;
iii. providing at least a first particulate filter layer to the inside of the casing and in contact with the gas filter layer; and
iv. applying a force to the first particulate filter layer thereby causing a force to be applied to the gas filter layer, fixing said gas filter layer in place.

The method may comprise the further steps of:

i. providing a first perforated support plate to the inside of the casing;
ii. providing a support layer to the inside of the casing and in contact with the first perforated support plate and the gas filter layer; and
iii. providing a second perforated support plate to the inside of the casing and in contact with the particulate filter layer.

The force may be applied to the second perforated support plate, which applies a force to the first particulate filter layer thereby causing a force to be applied to the gas filter layer, fixing said gas filter layer in place.

The force applied may cause the particulate filter layer to compress and to apply a force on the gas filter layer.

The force applied may be approximately 50 kg (490 N).

The method may comprise the further step of reversibly attaching the casing to a support surface.

Therefore, in one aspect, the invention describes a means by which single or double-sided filter units comprising gas (vapour) and particulate filters can be manufactured reliably, and where the particulate filter has been compressed to form a "spring" which locks the adsorbents/absorbents (i.e., the gas filter layer) in place.

According to a ninth aspect of the invention there is provided a filter unit manufactured by the method of the eighth aspect.

BRIEF DESCRIPTION OF THE DRAWINGS

There will now be described, by way of example only, embodiments of the invention with reference to the following Figures, of which:

FIG. 1 shows a plan view of a respiratory protective device including a filter box assembly;

FIG. 2 is a sectional view of a side elevation of a respiratory protective device including a filter box assembly;

DETAILED DESCRIPTION

Figure 3:
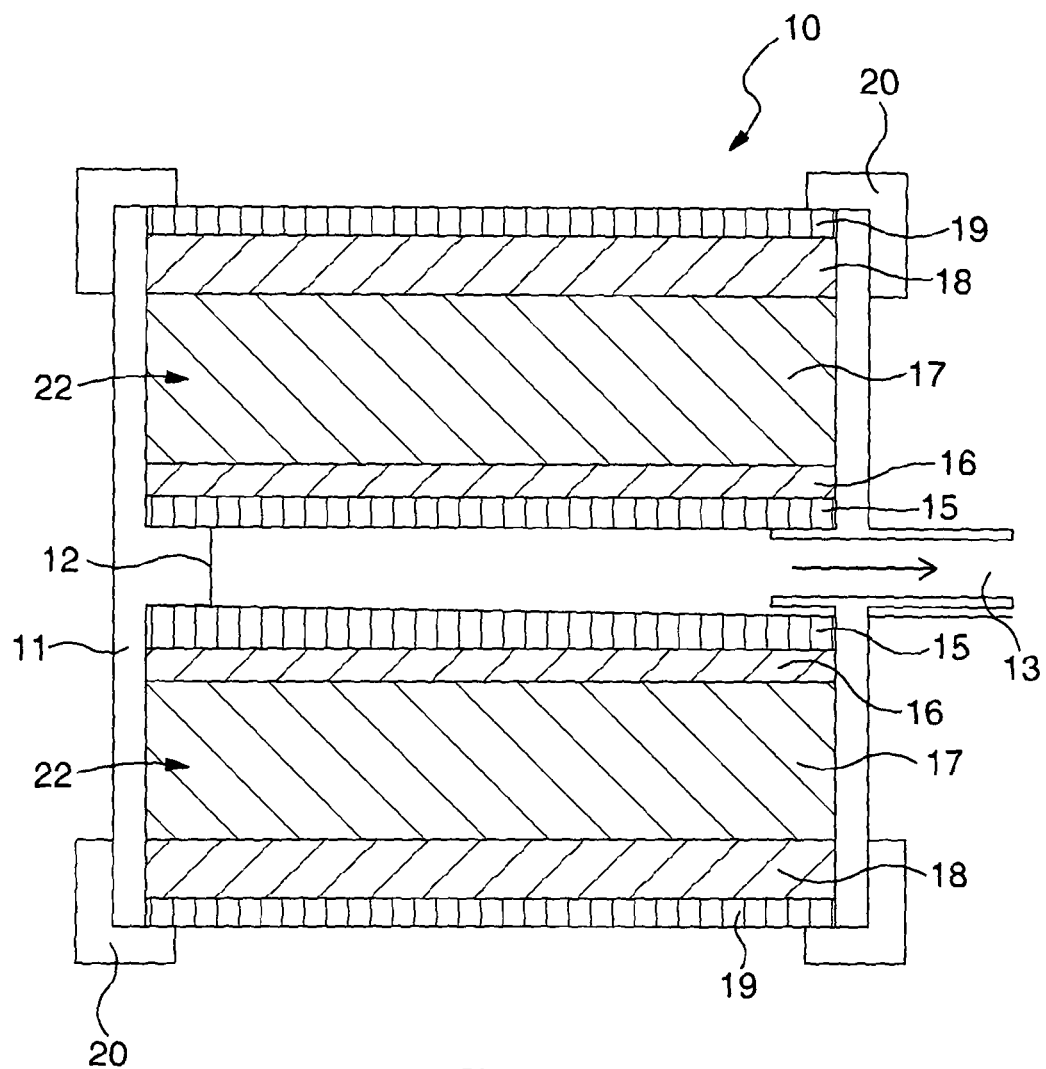
FIG. 3 shows a sectional view of a side elevation of a filter box assembly comprising two filter units.

Referring to FIG. 1, there is shown a respiratory protective device 30 having a filter box assembly 10 connected to a mouthpiece 24. Also shown are a perforated filter plate 19 and a nose clip 26.

Referring now to FIG. 2, there is shown there is shown a respiratory protective device 30 having a filter box assembly 10 connected to a mouthpiece 24. The filter box assembly contains two filter units 22 which share a common air channel 13. As can be seen, the air channel 13 is in direct contact with the filter units 22, and in this case is in direct contact with a support scrim (support layer) 16, which is a particulate filter. Adjacent the support scrim 16 is a gas filter layer 17, and adjacent the gas filter layer 17 is a particulate filter later 18. To the outside of the assembly 10 is a perforated filter plate 19 which is adjacent the particulate filter layer 18. Also shown is a nose clip 26.

In this embodiment, the filter unit 22 comprises the support scrim (support layer) 16, the gas filter layer 17, the particulate filter later 18, and the perforated filter plate 19. The casing 11 can also form part of the filter unit 22.

The gas filter layer 17 may be made from several components such as, for example, an activated charcoal powder or granules, which require to be held in place to prevent escape or leakage of the components.

In use, the wearer puts the mouthpiece 24 into their mouth, and the nose clip 26 over their nose, and thus can only breathe air which has passed through the filter box assembly 10 and, in particular, the filter units 22. The perforated filter plates 19 allow the ingress of atmospheric air. Any harmful particulates are removed by the particulate filter layers 18, 16, and any harmful gases and vapours are removed by the gas filter layers 17. Thus, contaminant free air is provided to the wearer.

Figure 4:
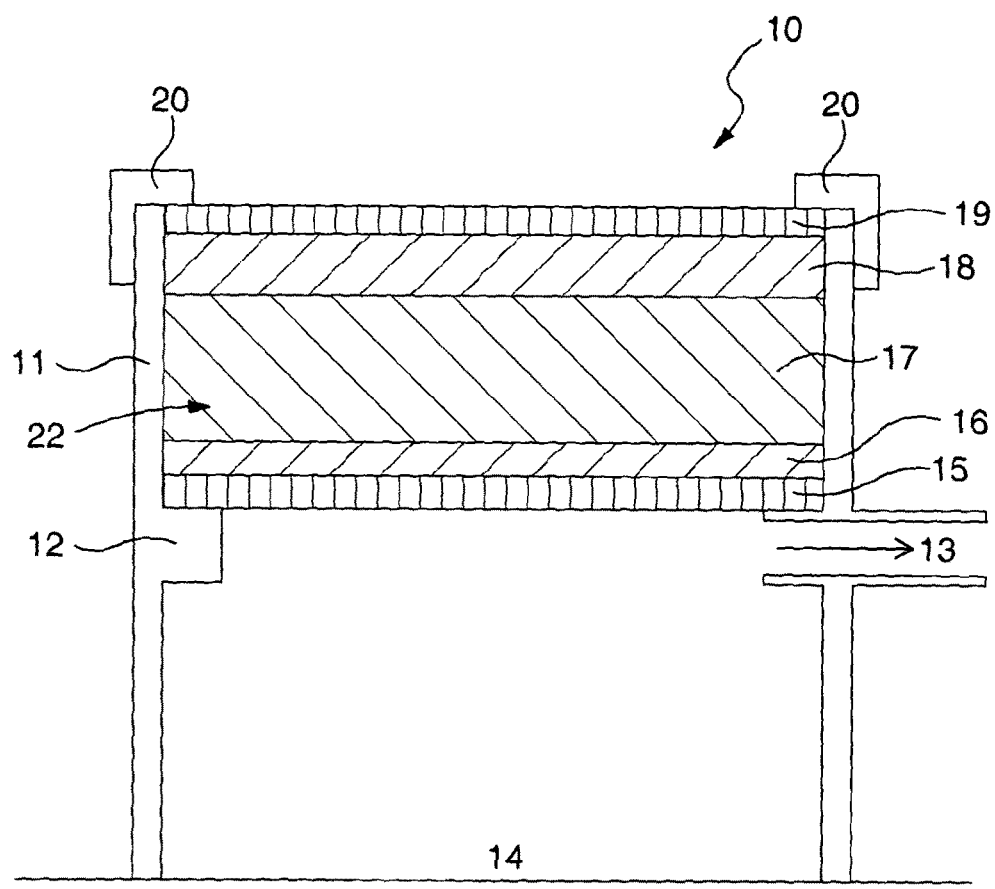
FIG. 4 shows a sectional view of a side elevation of a filter box assembly comprising one filter unit.

Referring now to FIGS. 3 and 4, there is illustrated a section through a double-sided (FIG. 3) and a partially completed (FIG. 4) filter box assembly 10 which is contained within casing 11 which incorporates a central step 12 and an outlet channel 13. The casing 11 can be of rigid or flexible form, and can be constructed from a suitable material, such as light alloy, nylon, ABS or "rubber", and can be of any suitable shape, such as round or rectanguloid. Casing 11 is designed to have sufficient strength to protect its contents, to withstand any forces imposed on the filter components, to withstand foreseeable forces that may be generated if the device is dropped onto hard surfaces, and to withstand foreseeable mishandling and rough usage.

The filter box assembly contains two filter units 22 which share a common air channel 13. As can be seen, the air channel 13 is in direct contact with the filter units 22, and in this case is in direct contact with a perforated filter plate 15. Adjacent the perforated support plate is a support scrim 16, which in this case is a particulate filter layer. Adjacent the support scrim 16 is a gas filter layer 17, and adjacent the gas filter layer 17 is a particulate filter layer 18. To the outside of the assembly 10 is a perforated filter plate 19 which is adjacent the particulate filter layer 18. Also shown is a lid 20, which can be used to locate nose clip 26.

In these embodiments, the filter unit 22 comprises the perforated filter plate 15, the support scrim (support layer) 16, the gas filter layer 17, the particulate filter later 18, and the perforated filter plate 19. The casing 11 can also form part of the filter unit 22.

Referring now to FIG. 4, there is illustrated a section through a filter box assembly 10 with one filter unit 22 assembled. To complete one half of the filter box assembly 10 (i.e., one filter unit 22), casing 11 is sat on, and temporarily sealed (i.e., reversibly attached) to rigid base 14, which acts as a support surface. Perforated filter plate 15 is sat on the top of central step 12. Support scrim 16 is sat on top of perforated filter plate 15 and a defined volume of adsorbent/absorbent 17 is "snowed" into the volume formed by support scrim 16 and the upper walls of the casing 11 so-forming a gas filter layer 17. Support scrim 16 may optionally provide a degree of filtration efficiency to capture particulates that may be released by adsorbent/absorbent 17, as such particulates can cause discomfort to the wearer.

The particulate filter 18 and perforated support plate 19 are sat sequentially on top of adsorbent/absorbent 17. A suitable force is then applied to perforated support plate 19 to cause particulate filter 18 to compress and so form the source of the force applied to adsorbent/absorbent 17 to lock them securely in position. A force of about 50 kg (490 N) has been found to be suitable for one widely used electrostatic filter medium, which is formed from suitable synthetic fibres, such as polypropylene.

A jig, not shown, may be required to ensure that during the compression of the particulate filter 18, the perforated filter plate 19 is correctly located to sit correctly within the lip of the casing 11. The perforated filter plate 19 is held securely in place by lid 20. Perforated filter plates 15, 19 can be identical, if desired. Laser cut stainless steel has been found to be a suitable material for forming perforated filter plates 15, 19. The perforated filter plates 19 may also act as and be referred to as support plates or perforated support plates. The perforated filter plates 15, 19 have sufficient structural strength and/or rigidity to support the pressure generated by the force applied to compress the particulate filters 16, 18. Furthermore, perforated filter plates 15, 19 have sufficient structural strength to retain their structural integrity when such forces are applied to them.

The central step 12 is sufficiently rigid to enable the height "h" of the central step 12 to be maintained under the load imposed by compression of the particulate filters 18. The central step 12 acts as a spacer, spacing the two filter units apart and can be a tab which is attached or integral to the casing 11, or can be a separate shim or spacer(s).

To complete the second half of the filter box assembly 10 (i.e., to add the second filter unit 22), the casing 11 is detached from the support surface 14, is turned upside down and is again reversibly attached to the support surface 14 so that the lid 20 sits on top of, and is temporarily sealed to, the support surface (rigid base) 14, and the above assembly procedure is repeated in the same sequence to achieve a complete double-sided filter box assembly 10.

It will be appreciated that the method described can be truncated to make a single filter unit and/or a single filter assembly.

Referring again to FIG. 3, there is illustrated a section through a completed filter box assembly 10. The contaminated air enters the filter assembly 10 through the particulate filters 18 before entering adsorbent/absorbent 17.

Lids 20 can be formed by swaging the top of casing 11 if it is made from metal or a suitable plastic. Alternatively it can be clipped, glued or welded in position if made from metal, plastic or rubber.

To ensure that both filter units 22 of the double-sided filter assembly 10 are as similar as possible in terms of breathing resistance, and therefore in terms of the volume of air flowing through each half of the filter assembly 10 in use, air at a defined flow rate can be drawn through outlet channel 13, and the pressure drop generated by each filter unit 22 can be measured sequentially using a suitable pressure measuring means, not shown. If necessary, a volume of adsorbent/absorbent 17 can be carefully snowed onto or removed from the second filter unit 22 as required before the second lid 20 is fixed in position.

The filter assemblies can be temporarily sealed to the support surface if it is wished to test the flow resistance of each filter unit.

In one embodiment the central step is an integral part of the casing wall. The central step abuts the perforated support plates on either side of the air channel, and defines the air channel depth.

In an alternative embodiment the central step is not an integral part of the casing wall, but is formed by a separate spacer, or spacers, located between the perforated support plates on either side of the air channel. In this embodiment the lid on the filter unit which is closest to the rigid base can be part of the casing, and the filter unit can be assembled by sequentially inserting the following parts into the casing: the first (lower) perforated support plate, the (lower) particulate filter, the (lower) gas layer, the (lower) support scrim, the second (lower) perforated support plate, the spacer, or spacers (which could be in the form of a topless and bottomless box which forms the sides of the air channel), the first (upper) support plate, the (upper) support scrim, the (upper) gas layer, the (upper) particulate filter and the second (upper) perforated support plate. The whole filter assembly can then be compressed as one unit to fix the gas filter layer in place before the top lid is then fitted.

The use of the compressed particulate filter to lock the adsorbent/absorbent granules in place can also be used in the manufacture of conventional combined gas and vapour and particulate filters.

Suitable materials for use in the particulate filter layer(s) include, for example, polypropylene or nylon.

Suitable materials for use in the gas filter layer include(s), for example, activated carbon, silica gel, molecular sieves or Tenax (Trade Mark).

Suitable materials for use in the support scrim include(s), for example, polypropylene or nylon.

This invention applies primarily to the manufacture of filter assemblies for respiratory protective devices, but can also be applied to the manufacture of filters for other applications.

While this invention has been described with reference to the sample embodiments thereof, it will be appreciated by those of ordinary skill in the art that modifications can be made to the structure and elements of the invention without departing from the spirit and scope of the invention as a whole.

What is claimed is:

1. A filter box assembly for use with a respiratory protective device, the filter box assembly comprising: a first filter unit and a second filter unit, wherein the first filter unit and the second filter unit share a common air channel in fluid contact with the first filter unit and the second filter unit, wherein the common air channel is adjacent to the first filter unit and the second filter unit, the first filter unit and the second filter unit comprising a gas filter layer and a first particulate filter layer, the first particulate filter layer comprising a resilient material, wherein the first particulate filter layer is compressed such that it applies a positive force against the gas filter layer, the first particulate filter layer thereby being configured to bias towards the gas filter layer.

2. The filter box assembly of claim 1, wherein the common air channel is located between the first filter unit and the second filter unit.

3. The filter box assembly of claim 1, further comprising a spacer configured to space apart the first filter unit and the second filter unit, wherein optionally the depth of the common air channel is defined by the spacer.

4. The filter box assembly of claim 1, wherein the filter unit comprises a support layer, which optionally is a second particulate filter layer.

5. The filter box assembly of claim 4, wherein the gas filter layer is located between the first particulate filter layer and the support layer.

6. The filter box assembly of claim 4, wherein the gas filter layer is adjacent to the first particulate filter layer and the support layer.

7. The filter box assembly of claim 1, wherein the filter unit comprises a first perforated support plate and a second perforated support plate.

8. The filter box assembly of claim 7, wherein the first particulate filter layer is located between the first perforated support plate and the second perforated support plate.

9. The filter box assembly of claim 7, wherein the first particulate filter layer is adjacent to one of the first perforated support plate and the second perforated support plate.

10. The filter box assembly of claim 7, wherein a support layer is located between the first perforated support plate and the second perforated support plate.

11. The filter box assembly of claim 10, wherein the support layer is adjacent to one of the first perforated support plate and the second perforated support plate.

12. A respiratory protective device comprising a filter box assembly as described in claim 1.

* * * * *